US007271194B2

(12) United States Patent
Sanchez et al.

(10) Patent No.: US 7,271,194 B2
(45) Date of Patent: *Sep. 18, 2007

(54) TREATMENT OF NEUROTIC DISORDERS

(75) Inventors: Connie Sanchez, Glostrup (DK);
Sandra Hogg, Frederiksberg (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 10/021,126

(22) Filed: Dec. 12, 2001

(65) Prior Publication Data

US 2002/0086899 A1 Jul. 4, 2002

Related U.S. Application Data

(63) Continuation of application No. PCT/DK00/00377, filed on Jul. 7, 2000.

(30) Foreign Application Priority Data

Jul. 8, 1999 (DK) ............... 1999 00991

(51) Int. Cl.
*A61K 31/34* (2006.01)
*A61K 31/335* (2006.01)

(52) U.S. Cl. .................... 514/467; 514/469

(58) Field of Classification Search ........... 514/469; 549/467

See application file for complete search history.

(56) References Cited

U.S. PATENT DOCUMENTS

| 3,467,675 | A | 9/1969 | Petersen et al. ......... 260/346.2 |
| 4,136,193 | A | 1/1979 | Bogeso et al. ............ 424/285 |
| 4,650,884 | A | 3/1987 | Bogeso ................. 549/467 |
| 4,902,710 | A | 2/1990 | Foster et al. |
| 4,943,590 | A | 7/1990 | Boegesoe et al. ........... 514/469 |
| 4,962,128 | A | 10/1990 | Doogan et al. |
| 5,114,976 | A | 5/1992 | Norden |
| 5,296,507 | A | 3/1994 | Tanaka et al. ............ 514/465 |
| 5,627,196 | A | 5/1997 | Audia et al. |
| 5,648,396 | A | 7/1997 | Young et al. |
| 5,788,986 | A | 8/1998 | Dodman |
| 5,958,429 | A | 9/1999 | Wong |
| 5,962,514 | A | 10/1999 | Evenden et al. |
| 6,069,177 | A | 5/2000 | Carlier et al. |
| 6,147,072 | A | 11/2000 | Bymaster et al. |
| 6,159,971 | A | 12/2000 | Berg et al. |
| 6,169,105 | B1 * | 1/2001 | Wong et al. ............ 514/415 |
| 6,184,219 | B1 | 2/2001 | Evenden et al. |
| 6,333,357 | B1 | 12/2001 | Eig |
| 6,469,064 | B2 | 10/2002 | Druzgala |
| 2002/0103249 | A1 | 8/2002 | Lundbeck |

FOREIGN PATENT DOCUMENTS

| EP | 0 347 066 A1 | 12/1989 |
| EP | 0474580 | 3/1992 |
| EP | 0 714 663 A2 | 6/1996 |
| EP | 0 759 299 | 2/1997 |
| EP | 0 814 084 A1 | 12/1997 |
| WO | WO92/18005 | 10/1992 |
| WO | WO93/09769 | 5/1993 |
| WO | WO-96/24353 A1 | 8/1996 |
| WO | WO-99/14207 A1 | 3/1999 |
| WO | WO 00/02551 | 1/2000 |
| WO | WO 00/03701 | 1/2000 |
| WO | 0015220 | 3/2000 |
| WO | WO 00/15219 | 3/2000 |
| WO | WO 00/15220 | 3/2000 |
| WO | 0034263 | 6/2000 |
| WO | WO-01/03694 A1 | 1/2001 |
| WO | WO 01/54681 A2 | 8/2001 |

OTHER PUBLICATIONS

A.F. Joubert et al., "Citalopram and Anxiety Disorders," *Rev. Contemp. Pharmacother* 10: 79-131 (1999).
Ulla M. Lepola et al., "A Controlled, Perspective, 1-Year Trial of Citalopram in the Treatment of Panic Disorder," *J. Clin. Psychiatry* 59, 10: 528-534 (1998).
H. Koponen et al., "Citalopram in the treatment of obsessive-compulsive disorder: an open pilot study," *Acta Psychiatrica Scandinavica* 96: 343-346 (1997).
Dan J. Stein et al., "Use of serotonin selective reuptake inhibitor citalopram in obsessive-compulsive disorder," *Journal of Serotonin Research* 1: 29-33 (1996).
Bigler, Allan et al., "Quantitative Structure-activity Relationships in a Series of Selective 5-HT uptake inhibitors," *Eur. J. Med. Chem.* 3:289-295 (1997).
Soraya Seedat et al., "Open trial of citalopram in adults with post-traumatic stress disorder," *International Journal of Neuropsychopharmacology* 3: 135-140 (2000).

(Continued)

*Primary Examiner*—Ardin H. Marschel
*Assistant Examiner*—Shirley V. Gembeh
(74) *Attorney, Agent, or Firm*—Darby & Darby

(57) ABSTRACT

Use of escitalopram (the S-(+)-enantiomer of citalopram) or a pharmaceutically acceptable salt thereof for the preparation of a medicament useful in the treatment of neurotic disorders is provided, including anxiety states, in particular generalised anxiety disorder and social anxiety disorder, post traumatic stress disorder, obsessive compulsive disorder and panic attacks.

25 Claims, No Drawings

OTHER PUBLICATIONS

Ihoko Muraki et al., "Effect of subchronic lithium carbonate treatment on anxiolytic-like effect of citalopram and MKC-242 in conditioned fear stress in the rat," European Journal of Pharmacology 383: 223-229 (1999).

Jennifer Y. Tan et al., "Citalopram in the Treatment of Depression and Other Potential Uses in Psychiatry," Pharmacotherapy 19, 6: 675-689 (1999).

Mario Amore et al., "Short-Term and Long-Term Evaluation of Selective Serotonin Reuptake Inhibitors in the Treatment of Panic Disorder: Fluoxetine vs Citalopram," Hum. Psychopharmacol. Clin. Exp. 14: 435-440 (1999).

Emanuela Mundo, M.D. et al., "Efficacy of Fluvoxamine, Paroxetine, and Citalopram in the Treatment of Obsessive-Compulsive Disorder: A Single-Blind Study," Journal of Clinical Psychopharmacology 17, 4: 267-271 (Aug. 1997).

Zoltan Rihmer, "Successful treatment of salbutamol-induced panic disorder with citalopram," European Neuropsychopharmacology 7: 241-242 (1997).

Takeshi Inoue et al., "Effect of citalopram, a selective serotonin reuptake inhibitor, on the acquisition of conditioned freezing," European Journal of Pharmacology 311: 1-6 (1996).

U. Lepola et al., "Citalopram in the Treatment of Early-onset Panic Disorder and School Phobia," Pharmacopsychiatry 29: 30-32 (Jan. 1996).

J. Hyttel et al., "The Pharmacology of Citalopram," Rev. Contemp. Pharmacother. 6: 271-285 (1995).

American Psychiatric Association, "DSM-IV" (Diagnostic and Statistical Manual of Mental Disorders, Fourth Edition): 393-444 (1994).

P. Auquier et al., *Int. J.Psychiatr. Clin. Pract.* 7:259-268 (2003).

E. Bien et al., *Behav. Pharmacol.* 14:S37 (2003).

E. W. Fish et al., *J. Pharmacol. Exp. Ther.* Oct. 30, 2003, Fast Forward publ. as DOI: 10.1124/jpet.103.058206 (2004).

C. Sanchez et al., *Physchopharmacology* 167:353-362 (2003).

C. Sanchez, *Behav. Pharmacol.* 14:465-470 (2003).

C. Sanchez et al. *Phychopharmacology (Berl).* (2004), "Escitalopram versus citalopram: the surprising role of the R-enantiomer".

Declaration of Connie Sanchez. (2005).

Hytell, J., Prog. Neuro-Psychopharmocol. & Biol. Psychiat., 1982, 6, 277-295.

Gravem, A., Acta Psychiatr. Scand., 1987, 75, 478-486.

Sanchez, C., Effect of serotonergic drugs on footshock-induced ultrasonice vocalization in adult male rats, Behav. Pharmacol. 1993; 4:267-277.

Sanchez, C., Pharmacol. Toxicol. 77, 71-78 (1995).

Sanchez, C. , R-citaloram attenuates anxiolytic effects of escitalopram in a rat ultrasonic vocalisation model, European Journal of Pharmacology, 464, 2003, pp. 155-158.

Montgomery,S., et al., Escitalopram (S-Enantiomer of Citalopram): Clinical Efficacy and Onset of Action Predicted from a Rat Model, Pharmacology & Toxicology, 2001, 88, 282-286.

Sanchez,C., Stress-induced vocalisation in adult animals: A valid model of anxiety?,European Journal of Pharmacology, 463 (2003) 133-143.

Burke, W., et al., Fixed-Dose Trial of the Single Isomer SSRI Escitalopram in Depressed Outpatients, J. Clin Psychiatry, 63:4, Apr. 2002.

Wade, A., et al., Escitalopram 10 mg/day is effective and well tolerated in a placebo-controlled study in depression in primary care, International Clinical Psychopharmacology 2002, vol. 17, No. 3.

Stahl et al., J. Clin. Psychiatry 2003; 64:1322-1327.

Sackeim, H.A., The definition and meaning of treatment-resistant depression, J. Clin. Psychiatr 2001, 62 Suppl 16, 10-17.

Willner, P., Psychopharmacology, 1997, 134, 319-329.

Nierenber, A.A. and DeCecco, L.M., Definitions of antidepressant treatment response, remission, non-response, partial response, and other relevant outcomes: A focus on treatment-resistant depression, J. Clin. Psychiatr 2001, 62 Suppl 16, 5-9.

Kornstein, S.C. and Schneider, R.K., Clinical features of treatment-resistant depression, J. Clin. Psychiatr 2001, 62 Suppl 16, 18-25.

Poster, Escitalopram and Paroxetine in Fixed Doses for the Treatment of Social Anxiety Disorder (SAD), Presented at the 44th Annual Meeting of the Scandinavian College of Neuro-Psychopharmacology, Apr. 9-12, 2003, Juan-les-Pins, France, 1 page.

Kasper, Siegfried, et al., "Escitalopram is Efficacious and well Tolerated in Treatment of Social Anxiety Disorder", ADAA National Conference, Mar. 21-24, 2002, 1 page.

Davidson, Jonathan, et al., "Escitalopram in the Treatment of Generalized Anxiety Disorder", Presented at the 22nd National Conference of the Anxiety Disorder Association of America, Mar. 21-24, 2002, Austin, Texas, NR57, 1 page.

Stahl, Stephen, et al., "Escitalopram in the Treatment of Panic Disorder", Presented at the 22nd National Conference of the Anxiety Disorders Association of America, Mar. 21-24, 2002, Austin, Texas, NR56, 1 page.

Lader, Malcolm, et al., "Efficacy and Tolerability of Escitalopram in 12- and 24-Week Treatment of Social Anxiety Disoder: Randomised, Double-Blind, Placebo-Controlled, Fixed-Dose Study", Depression and Anxiety, 19: 241-248 (2004).

Huffman, Jeff C., et al., "The Development of New Antidepressants: Focus on Duloxetine and Escitalopram", Harv Rev Psychiatry, 11:30-36 (2003).

Waugh, John, et al., "Escitalopram, A review of its Use in the Management of Major Depressive and Anxiety Disorders", CNS Drugs, 17 (5): 343-362 (2003).

Burke, William J., "Escitaiopram", Expert Opin. Investig. Drugs, 11(10): 1477-1486 (2002).

Farah, Andrew, "Therapeutic Advantages of Escitalopram in Depression and Anxiety Disorders", Primary Psychiatry, 9(12): 30-35 (2002).

Montgomery, S.A., et al., "The antidepressant efficacy of citalopram", International Clinical Psychopharmacology (1996), vol. 11, Supplement 1, pp. 29-33.

Bouchard, J.M., et al., "Citalopram and Viloxazine in the treatment of depression by means of slow drop infusion: A double-blind comparative trial", Journal of Affective Disorders, vol. 46, pp. 51-58 (1997).

Declaration of Connie Sanchez.

Hyttel, J., et al., "The pharmacological effect of citalopram resides in the (S)—(+)-enantiomer", Journal of Neural Transmission, 1992, vol. 88, No. 2, pp. 157-160.

Sanchez, Connie, et al., "Behavioral profiles of SSRIs in animal models of depression, anxiety and aggression", Psychopharmacology, 1997, vol. 129, pp. 197-205.

Lepola U., et al., "Citalopram in the Treatment of Social Phobia: A Report of Three Cases", Pharmacopsychiatry, Sep. 1994, vol. 27, No. 5, pp. 186-188.

Humble, M., et al., "Serotonin, Panic Disorder and Agoraphobia: Short-Term and Long-Term Efficacy of Citalopram in Panic Disorders", International Clinical Psychopharmacology, 1992, vol. 6, No. suppl 5, pp. 21-39.

Bouwer, C., et al., "Use of the selective serotonin reuptake inhibitor citalopram in the treatment of generalized social phobia", Journal of Affective Disorders, Apr. 1998, vol. 49, No. 1, pp. 79-82.

Lepola et al., The effect of citalpram in panic disorder and agoraphobia, Nord, J. Psych., 1994, 48:13-17.

Lepola et al., Citalpram in Anxiety Disorder of Childhood and Adolescence, Eur. Child Adol. Psych., 1994, 3(4):277-279.

Ragneskog et al., Long-Term Treatment of Elderly Individuals With Emotional Disturbances: An Open Study With Citalopram, Int. Psychoger., 1996, 8(4):659-668.

Wade et al., The effect of citalpram in panic disorder, Br. J. Psychiatry, 1997, 170:549-553.

Sanchez et al., R-citalopram counteracts the effect of escitalopram in a rat conditioned fear stress model of anxiety, Pharm. Biol. Behav., 2003, 75:903-907.

* cited by examiner

TREATMENT OF NEUROTIC DISORDERS

This application is a continuation of PCT/DK00/00377, filed Jul. 7, 2000.

FIELD OF INVENTION

The present invention relates to the use of the compound escitalopram (INN-name), which is the S-enantiomer of the well-known antidepressant drug citalopram, i.e. (S)-1-[3-(dimethyl-amino)propyl]-1-(4-fluorophenyl)-1,3-dihydro-5-isobenzofurancarbonitrile, or a pharmaceutically acceptable salt thereof for the preparation of medicaments for the treatment of neurotic disorders, including anxiety states and panic attacks.

BACKGROUND OF THE INVENTION

Citalopram is a well-known antidepressant drug that has now been on the market for some years and has the following structure:

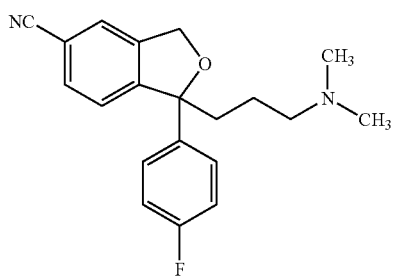

Formula I

It is a selective, centrally acting serotonin (5-hydroxytyptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277-295 and A. Gravem, *Acta Psychiatr. Scand.*, 1987, 75, 478-486, and it is now marketed for the treatment of depression and panic disorders. The compound has further been disclosed to show effects in the treatment of dementia and cerebrovascular disorders, EP-A 474580.

Escitolopram and a method for its preparation are disclosed in U.S. Pat. No. 4,943,590. The stereo selectivity of citalopram, i.e. the 5-HT-reuptake inhibition in the S-enantiomer, and accordingly, the antidepressant effect of said enantiomer is also disclosed. S-citalopram is now in development as an antidepressant.

Studies have shown that patients suffering from neurotic disorders including anxiety disorders, especially generalised anxiety, and panic attacks, in particular in association with agoraphobia, have a quality of life impairment comparable with or greater than the disability found in patients with alcoholism, schizophrenia or personality disorders. Furthermore, current treatments are not always effective or cause unacceptable side effects.

Consequently, there is a need for alternative therapies useful in the treatment of neurotic disorders.

Escitalopram has now been found to show potent effects in models of neurotic disorders such as anxiolytic effect and prominent effect in the treatment of panic attacks and obsessive compulsive disorder.

DESCRIPTION OF THE INVENTION

According to the present invention, a novel use of escitalopram, namely for the preparation of a medicament useful in the treatment of neurotic disorders is provided.

Throughout this specification and claims the term neurotic disorders is used to designate a group of mental disorders, including anxiety states, in particular generalised anxiety disorder and social anxiety disorder, post traumatic stress disorder, obsessive compulsive disorder and panic attacks.

The terms generalised anxiety disorder, social anxiety disorder, post traumatic stress disorder and obsessive compulsive disorder are as defined in DSM IV.

The phrase "panic attacks" contemplates treatment of any disease, which is associated with panic attacks including panic disorder, specific phobias, social phobia and agoraphobia in which panic attacks occur. These disorders are further defined in the DSM IV. A panic attack is a discrete period in which there is a sudden onset of intense apprehension, fearfulness or terror, often associated with feelings of impending doom. During the attack, symptoms such as palpitations, sweating, trembling, sensations of shortness of breath, feeling of choking, chest pain or discomfort, nausea, feeling dizzy, feelings of unreality, fear of losing control or going crazy, fear of dying, paresthesias and chills or hot flushes are present.

Panic disorders are characterised by recurrent unexpected panic attacks about which there is a persistent concern. Agoraphobia is anxiety about, or avoidance of, places or situations from which escape might be difficult or in which help may not be available in the event of a panic attack. Specific phobia and social phobia (together formerly simple phobia) are characterised by marked and persistent fear that is excessive or unreasonable, cued by the presence or anticipation of a specific object or situation (flying, heights, animals, seeing blood etc.) or social performance situations.

The disorders in which panic attacks occur are differentiated from each other by the predictability of the occurrence of the attacks, for example, in panic disorder the attacks are unpredictable and not associated with any particular event, whereas in specific phobia the attacks are triggered by specific stimuli.

The phrase "treatment of panic disorder" means a reduction in the number or prevention of attacks and/or relief of the severity of the attacks. Similarly, the treatment of generalised anxiety disorder, social anxiety disorder, post traumatic stress disorder and obsessive compulsive disorder include the treatment or prevention of these diseases, or the relief of the symptoms thereof.

According to the invention, escitalopram may be used as the base of the compound or as a pharmaceutically acceptable acid addition salt thereof or as an anhydrate or hydrate of such salt. The salts of the compound used in the invention are salts formed with non-toxic organic or inorganic acids, in particular the oxalate.

Escitalopram has been found to show prominent effects different from the effects of the racemate in the "Inhibition of footshock-induced ultrasonic vocalisation in adult rats"—test, the "Mice Black and White Test" setup, and in the polydipsia test. These models are standard animal models for anxiolytic effect and effect on panic attacks and for obsessive compulsive disorder, respectively.

According to the invention, escitalopram or a pharmaceutically acceptable salt thereof may be administered in any suitable way e.g. orally or parenterally, and it may be presented in any suitable form for such administration, e.g. in the form of tablets, capsules, powders, syrups or solutions or dispersions for injection. Preferably, and in accordance with the purpose of the present invention, the compound of the invention is administered in the form of a solid pharmaceutical entity, suitably as a tablet or a capsule or in the form of a suspension, solution or dispersion for injection.

Methods for the preparation of solid pharmaceutical preparations are well known in the art. Tablets may thus be prepared by mixing the active ingredients with ordinary adjuvants and/or diluents and subsequently compressing the mixture in a convenient tabletting machine. Examples of adjuvants or diluents comprise: corn starch, lactose, talcum, magnesium stearate, gelatine, lactose, gums, and the like. Any other adjuvant or additive such as colourings, flavourings, preservatives, etc. may also be used provided that they are compatible with the active ingredients.

The compound of the invention is most conveniently administered orally in unit dosage forms such as tablets or capsules, containing the active ingredient in a dose from about 1.0 mg to 50 mg, preferably 5 mg/day to 40 mg/day, most preferably 10 mg/day to 20 mg/day.

The oxalate of escitalopram may be prepared as described in U.S. Pat. No 4,943,590 and the base and other pharmaceutically acceptable salts may be obtained therefrom by standard procedures.

Thus the acid addition salts used according to the invention may be obtained by treatment of escitalopram with the acid in an inert solvent followed by precipitation, isolation and optionally re-crystallisation by known methods and if desired micronisation of the crystalline product by wet or dry milling or another convenient process, or preparation of particles from a solvent-emulsification process.

Pharmacological Tests

Escitalopram was tested in well recognised and reliable test models of effects on neurotic disorders. Citalopram-racemate was included for comparison purposes.

The Footshock-induced Vocalisation Test in Adult Rats.

The footshock-induced vocalisation test in adult rats (described in detail in Sánchez C., Effect of serotonergic drugs on footshock-induced ultrasonic vocalization in adult male rats. *Behav. Pharmacol.* 1993; 4:267-277) is a test for anxiolytic and anti-panic effects.

Experimental Procedure

Male rats (Wistar WU, Charles River, Germany), weighing 150-175 g at the beginning of the study were used.

Briefly, test cages (22 cm×22 cm×22 cm) made of grey Perspex and equipped with a metal grid floor were used. Footshocks were delivered from a two pole shocker and a microphone sensitive to ultrasounds in the range of 20-30 kHz was placed in the centre of the lid of the test cage. The ultrasounds were sent from the microphone to a preamplifier and converted from AC signals to DC signals in a signal rectifier. The accumulated time, in which the voltage of the rectified signal was larger than the voltage of a previously determined treshold level, was recorded.

Twenty-four hours before the first test session the animals were primed. A rat was placed in each test cage and received, immediately thereafter, four 1.0 mA inescapable footshocks each of a duration of 10 sec and with an intershock interval of 5 sec. The animals were left in the test cage for 6 min after the last shock. On test days, drug or saline was given 30 min before test. The rats received four 1.0 mA inescapable footshocks each of a duration of 10 sec. The intershock interval was 5 sec. Recording of ultrasonic vocalisation started 1 min after the last shock and lasted for 5 min. The total time spent on vocalisation was recorded. After a wash-out period of one week the rats were used in a new test session. The rats were used for a total of 7-8 weeks. At each test session, the animal groups were randomly allocated to treatment with saline or test drug. Each treatment group consisted of 8 animals, one saline and 2-4 drug treated groups were included at each session. Each drug was tested at least in two separate experiments with overlapping doses.

Results

The experiments showed that the maximum effect was 60-70% inhibition for citalopram-racemate whereas escitalopram was able to inhibit vocalisation completely.

Black and White Box Test

This is a test for anxiolytic effects. The test model is further described in Sánchez, C. (1995) Pharmacol. Toxicol. 77, 71-78.

Test Procedure

Male mice (Lundbeck strain, Charles River, Germany) weighing 30-35 g were housed in groups of 4 in macrolon cages type II under a reversed 12 h day /night cycle (lights off 7 p.m.). The mice were adapted to the reversed light/dark cycle for at least 3 weeks prior to testing. The room temperature (21±2° C.), relative humidity (55±5%), and air exchange (16 times per h) were automatically controlled. The animals had free access to commercial food pellets and water.

The test box used was designed as described by Sánchez (1995) (supra). Briefly, the test box (45 cm×27 cm×27 cm) was open-topped and divided into two compartments (ratio 2:3) by a partition which was black on the side facing the black compartment and white on the side facing the white compartment. The smaller chamber was made of black perspex. The larger chamber was made of white perspex except for the lowest 7.5 cm. This part was made of transparent perspex (outer walls) and black perspex (partition). The white compartment was connected to the black compartment by a 7.5 cm×7.5 cm opening in the partition. The floor of the white compartment was divided into 9 fields, and the floor of the black was divided into 6 fields. The white compartment was illuminated by means of a Schott KL 1500 electronic lamp emitting cold light corresponding to a light intensity of 560 Lux. The mouse test-system was fully automated by 2 rows of 11 infrared light sources and photocells in the transverse direction and 1 row of 16 in the longitudinal direction (lower row). The lower row of photocells (2 cm above cage floor) detected horizontal locomotor activity (crossing, entries, and time in each compartment), whereas the upper row of photocells (5 cm above cage floor) detected rearing activity. The accumulated data for 1 min intervals were recorded from 4 test boxed simultaneously and stored in a Paradox data base.

The test boxes were placed in a dark and quiet room. The mice were transported to the test room in a darkened container about 2 h before test. The test room was separated into two parts by a black curtain. The drug treatment took place in one part of the room using a minimum of red light. After dosing, the mice were placed individually in macrolon type cages until test. The pretreatment time was 30 min. The test boxes were placed in the other part of the room. The test was started by placing the mouse in the centre of the brightly-lit white compartment facing the opening to the black compartment. The test duration was 5 min and the number of rears and line crossings between squares in both the black and the white compartment, number of entries into the black compartment and time spent in the white compartment were assessed.

Results

Escitalopram showed prominent effects in this model.

Schedule-Induced Polydipsia

Food deprived rats exposed to a procedure in which food is delivered intermittently will drink large amounts of water if given the opportunity to do so. This behavioural phenomenon is called schedule-induced polydipsia and can be considered as an excessive expression of a normal behaviour. Schedule-induced polydipsia is regarded as a model of obsessive-compulsive disorder (Woods et al. 1993).

Test Procedure

Male wistar rats (Møllegard) housed in pairs and kept on a food-restricted diet (80% of normal body weight) for 2 weeks before the start of testing and throughout the duration of testing. To induce polydipsia rats were placed in test chambers where a pellet dispenser automatically dispensed one 60 mg food pellet every 60 seconds. Water was available at all times in the test chamber. Rats were tested 4-5 times per week, after 3-4 weeks training 70% of the rats were drinking >10 ml per 30 min test session.

Once the rats had attained a steady drinking level compounds could be tested. Citalopram (40 mg/kg) or Lu 26-054 (20 mg/kg) were administered orally 60 min prior to testing and at 10:00 on the non-test days. The water intake was presented as a percentage of the pre-dosing (baseline) level.

Results

Escitalopram produced a significant reduction in water intake, whereas citalopram was without effect.

All these studies show that escitalopram has potent anti neurotic diseases effects, in particular anxiolytic effects and effects on panic attacks and obsessive compulsive disorder.

What is claimed is:

1. A method of treating panic attacks in a patient in need thereof, said method comprising administration of a pharmaceutically effective amount of escitalopram or a pharmaceutically acceptable salt thereof to the patient.

2. The method of claim 1, wherein the pharmaceutically effective amount of escitalopram or a pharmaceutically acceptable salt thereof is in a unit dose form.

3. The method of claim 1, wherein the method comprises administering 1.0 to 50 mg/day of escitalopram or a pharmaceutically acceptable salt thereof.

4. The method of claim 1, wherein the method comprises administering 5 to 40 mg/day of escitalopram or a pharmaceutically acceptable salt thereof.

5. The method of claim 1, wherein the method comprises administering 10 to 20 mg/day of escitalopram or a pharmaceutically acceptable salt thereof.

6. The method of claim 1, wherein said panic attacks are associated with panic disorder.

7. The method of claim 1, wherein said panic attacks are associated with specific phobias.

8. The method of claim 1, wherein said panic attacks are associated with social phobia.

9. The method of claim 1, wherein said panic attacks are associated with agoraphobia.

10. The method of claim 6, wherein the pharmaceutically effective amount of escitalopram or a pharmaceutically acceptable salt thereof is in a unit dose form.

11. The method of claim 6, wherein the method comprises administering 1.0 to 50 mg/day of escitalopram or a pharmaceutically acceptable salt thereof.

12. The method of claim 6, wherein the method comprises administering 5 to 40 mg/day of escitalopram or a pharmaceutically acceptable salt thereof.

13. The method of claim 11, wherein the method comprises administering 10 to 20 mg/day of escitalopram or a pharmaceutically acceptable salt thereof.

14. The method of claim 7, wherein the pharmaceutically effective amount of escitalopram or a pharmaceutically acceptable salt thereof is in a unit dose form.

15. The method of claim 7, wherein the method comprises administering 1.0 to 50 mg/day of escitalopram or a pharmaceutically acceptable salt thereof.

16. The method of claim 7, wherein the method comprises administering 5 to 40 mg/day of escitalopram or a pharmaceutically acceptable salt thereof.

17. The method of claim 7, wherein the method comprises administering 10 to 20 mg/day of escitalopram or a pharmaceutically acceptable salt thereof.

18. The method of claim 8, wherein the pharmaceutically effective amount of escitalopram or a pharmaceutically acceptable salt thereof is in a unit dose form.

19. The method of claim 8, wherein the method comprises administering 1.0 to 50 mg/day of escitalopram or a pharmaceutically acceptable salt thereof.

20. The method of claim 8, wherein the method comprises administering 5 to 40 mg/day of escitalopram or a pharmaceutically acceptable salt thereof.

21. The method of claim 8, wherein the method comprises administering 10 to 20 mg/day of escitalopram or a pharmaceutically acceptable salt thereof.

22. The method of claim 9, wherein the pharmaceutically effective amount of escitalopram or a pharmaceutically acceptable salt thereof is in a unit dose form.

23. The method of claim 9, wherein the method comprises administering 1.0 to 50 mg/day of escitalopram or a pharmaceutically acceptable salt thereof.

24. The method of claim 9, wherein the method comprises administering 5 to 40 mg/day of escitalopram or a pharmaceutically acceptable salt thereof.

25. The method of claim 9, wherein the method comprises administering 10 to 20 mg/day of escitalopram or a pharmaceutically acceptable salt thereof.

* * * * *